US007605276B2

(12) United States Patent
Ito et al.

(10) Patent No.: US 7,605,276 B2
(45) Date of Patent: Oct. 20, 2009

(54) SPIROCYCLIC ACETAL COMPOUND AND METHOD OF PRODUCING THE SAME, AND POLYMER HAVING SPIROCYCLIC ACETAL STRUCTURE

(75) Inventors: Takayuki Ito, Minami-ashigara (JP); Sumiaki Yamasaki, Kanagawa (JP); Toshimitsu Sakuma, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 259 days.

(21) Appl. No.: 11/700,772

(22) Filed: Feb. 1, 2007

(65) Prior Publication Data

US 2007/0191584 A1 Aug. 16, 2007

(30) Foreign Application Priority Data

Feb. 2, 2006 (JP) ............................. 2006-026309
Sep. 29, 2006 (JP) ............................. 2006-269475

(51) Int. Cl.
*C07D 319/00* (2006.01)

(52) U.S. Cl. ...................................................... 549/335

(58) Field of Classification Search .................. 549/335
See application file for complete search history.

(56) References Cited

OTHER PUBLICATIONS

Grabhoefer et al, DN 63:94762 (1964).*
Kenner, DN 23:14124 (1928).*
Maslinska-Solich et al., Polymer International, vol. 52, pp. 1633-1640 (2003).
Jin et al., Synthetic Communications, vol. 29, No. 9, pp. 1601-1606, (1999).
M. Balog et al., Tetrahedron, vol. 60, pp. 4789, 4790 and 4795, (2004).
Clements et al., J. Org. Chem, vol. 24, pp. 1958-1961, (1959).
Zhang et al., J. Chem. Research (S), pp. 640-641, (1998).

* cited by examiner

*Primary Examiner*—Janet L Andres
*Assistant Examiner*—Raymond Covington
(74) *Attorney, Agent, or Firm*—Birch, Stewart, Kolasch & Birch, LLP

(57) ABSTRACT

A method of producing a spirocyclic acetal compound of formula (II), having subjecting a compound of formula (I) and pentaerythritol to dehydration condensation, in the presence of a solid acid catalyst; and the polymer having a repeating unit represented by formula (III), which is produced using the spirocyclic acetal compound of formula (II):

(I)

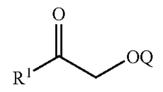

(II)

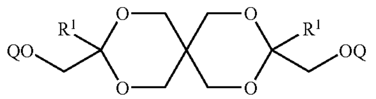

(III)

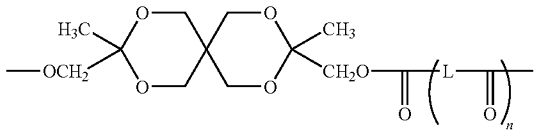

wherein $R^1$ represents an alkyl, cycloalkyl or aryl group, Q represents a hydrogen atom or an acyl group, L represents a divalent linking group having at least one carbon atom, and n is 0 or 1.

10 Claims, No Drawings

SPIROCYCLIC ACETAL COMPOUND AND METHOD OF PRODUCING THE SAME, AND POLYMER HAVING SPIROCYCLIC ACETAL STRUCTURE

FIELD OF THE INVENTION

The present invention relates to a novel spirocyclic acetal compound and a method of producing the same. The present invention also relates to a novel polymer having a repeating unit of spirocyclic acetal structure, and specifically to a novel diacrylate compound or polyester, which is produced, using the acetal compound.

BACKGROUND OF THE INVENTION 2,4,8,10-Tetraoxaspiro[5,5]undecanes having a hydroxyl or ester group directly or via an alkylene or phenylene group at the 3- or 9-position, are useful as starting materials for polymers with good workability, heat resistance, water resistance, mechanical strength, adhesion, anti-cracking properties, or the like, or useful as crosslinking agents for exhibiting these performances (or as starting materials for such crosslinking agents) (for example, see U.S. Pat. No. 2,945,008, JP-A-60-195168 ("JP-A" means unexamined published Japanese patent application), JP-A-61-47722, JP-A-61-195136, JP-A-2-187424, JP-A-4-88078, JP-A-2001-277421; Polymer (Korea), Vol. 4, No. 5, p. 448-455 (1990); and Polymer Int., Vol. 52, p. 1633-1640 (2003)).

In general, 2,4,8,10-tetraoxaspiro[5,5]undecanes can be synthesized by dehydration condensation of a carbonyl compound and pentaerythritol ($C(CH_2OH)_4$) in the presence of an acid catalyst (for example, see SYNTHETIC COMMUNICATIONS, Vol. 29, No. 9, p. 1601-1606 (1999); and Bull. Chem. Soc. Jpn., Vol. 75, p. 2195-2205 (2002)). A certain carbonyl compound having a hydroxyl or ester group in its molecule may be used as a starting material, to synthesize 2,4,8,10-tetraoxaspiro[5,5]undecanes that have a hydroxyl or ester group directly or via an alkylene or phenylene group at the 3- or 9-position and that are useful as starting materials for polymers or as crosslinking agents (or as starting materials for such crosslinking agents) (for example, see U.S. Pat. No. 3,092,640; Tetrahedron, 60, p. 4789-4800 (2004); and J. Org. Chem., Vol. 24, p. 1958-1961 (1959)).

In these cases, however, side reactions, such as self-condensation and transesterification, can occur at the same time. As shown in SYNTHETIC COMMUNICATIONS, Vol. 29, No. 9, p. 1601-1606 (1999), and Bull. Chem. Soc. Jpn., Vol. 75, p. 2195-2205 (2002), the target spirocyclic acetal-forming reaction is slow particularly in the case of ketones, as compared with the case of aldehydes, and thus it is not few that the target substance of high purity cannot be efficiently produced from the ketones.

For the purpose of solving this problem, there is a known synthesis in which a diketal (3,3,9,9-tetramethyl-2,4,8,10-tetraoxaspiro[5,5]undecane) is transiently prepared from acetone and pentaerythritol ($C(CH_2OH)_4$), and 3,9-dialkyl (or diaryl)-3,9-bis(methoxycarbonylalkyl)-2,4,8,10-tetraoxaspiro[5,5]undecane is synthesized in high yield and high purity by acetal exchange reaction of the diketal and a ketoester in methanol with an acid catalyst (J. Org. Chem., Vol. 26, p. 2515-2518 (1961)).

However, this method has a complicated process and a large number of steps, and thus is not economically preferred. Also in this method, the problem of side reactions, such as transesterification, is not substantially resolved. Thus, this method is not applicable in the synthesis of 3,9-dialkyl (or diaryl)-3,9-bis[acyloxymethyl (or hydroxymethyl)]-2,4,8,10-tetraoxaspiro[5,5]undecane.

As described above, hitherto, there is no known method of efficiently synthesizing 3,9-dialkyl (or dicycloalkyl or diaryl)-3,9-bis[acyloxymethyl (or hydroxymethyl)]-2,4,8,10-tetraoxaspiro[5,5]undecane. Thus, hitherto, 3,9-dimethyl-3,9-bis(hydroxymethyl)-2,4,8,10-tetraoxaspiro[5,5]undecane or a diacyl derivative thereof, and polyesters which are produced with a starting material of such a diol as 3,9-dimethyl-3,9-bis(hydroxymethyl)-2,4,8,10-tetraoxaspiro[5,5]undecane, are unknown.

SUMMARY OF THE INVENTION

The present invention resides in a method of producing a spirocyclic acetal compound represented by formula (II), which comprising the step of: subjecting a compound represented by formula (I) and pentaerythritol to dehydration condensation, in the presence of a solid acid catalyst, (I)

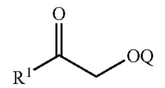

(II)

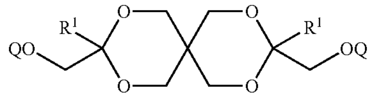

wherein $R^1$ represents an alkyl group, a cycloalkyl group or an aryl group, in which each of these groups may have a substituent; and Q represents a hydrogen atom or an acyl group.

Further, the present invention resides in a spirocyclic acetal compound represented by formula (A):

(A)

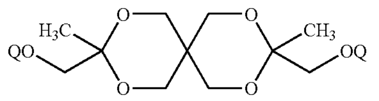

wherein Q represents a hydrogen atom or an acyl group.

Further, the present invention resides in a polymer having a repeating unit represented by formula (III):

(III)

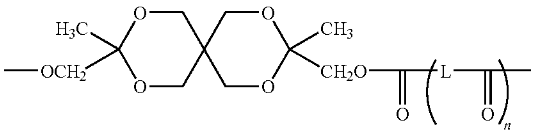

wherein L represents a divalent linking group having at least one carbon atom, and n represents 0 or 1.

Other and further features and advantages of the invention will appear more fully from the following description.

DETAILED DESCRIPTION OF THE INVENTION

According to the present invention, there is provided the following means:

(1) A method of producing a spirocyclic acetal compound represented by formula (II), comprising the step of:

subjecting a compound represented by formula (I) and pentaerythritol to dehydration condensation, in the presence of a solid acid catalyst, (I)

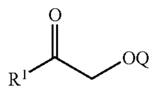

(II)

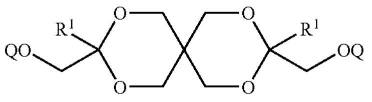

wherein $R^1$ represents an alkyl group, a cycloalkyl group or an aryl group, in which each of these groups may have a substituent; and Q represents a hydrogen atom or an acyl group;

(2) The method according to Item (1), wherein the solid acid catalyst is zeolite or a layered clay mineral;

(3) The method according to Item (1) or (2), wherein the solid acid catalyst is a layered clay mineral;

(4) The method according to Item (2) or (3), wherein the layered clay mineral is montmorillonite;

(5) The method according to any one of Items (1) to (4), wherein $R^1$ is a methyl group;

(6) A spirocyclic acetal compound represented by formula (A):

(A)

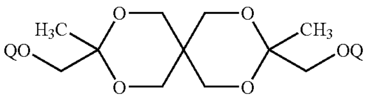

wherein Q represents a hydrogen atom or an acyl group, and Q preferably represents a hydrogen atom, $-COCH_3$, $-COC_2H_5$, $-COCH{=}CH_2$, or $-COC(CH_3){=}CH_2$;

(7) The spirocyclic acetal compound according to Item (6), wherein the compound represented by formula (A) is a compound represented by any one of formulae (II-1), (II-2) and (II-3);

(II-1)

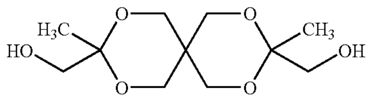

(II-2)

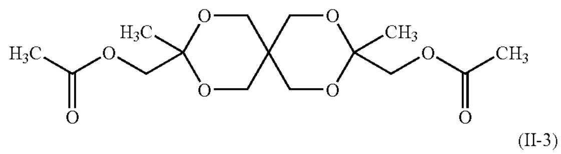

(II-3)

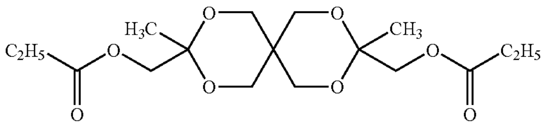

(8) The spirocyclic acetal compound according to Item (6), wherein the compound represented by formula (A) is a compound represented by formula (II-4):

(II-4)

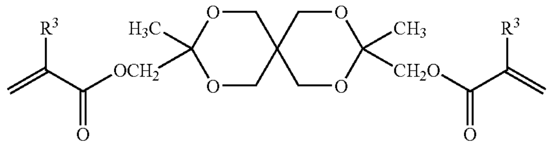

wherein $R^3$ represents a hydrogen atom or a methyl group; and (9) A polymer having a repeating unit represented by formula (III):

(III)

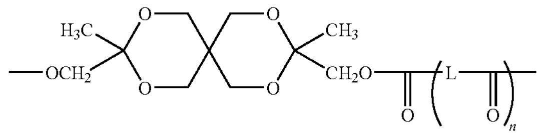

wherein L represents a divalent linking group having at least one carbon atom, and n represents 0 or 1.

The present invention will be explained in detail hereinafter.

First, the spirocyclic acetal compound represented by formula (II) is described.

In the compound represented by formula (II), $R^1$ represents an alkyl, cycloalkyl, or aryl group. The alkyl group for $R^1$ preferably has 1 to 20 carbon atoms, and more preferably 2 to 10 carbon atoms, and may be linear or branched. The cycloalkyl group for $R^1$ preferably has 3 to 20 carbon atoms, and more preferably 5 to 10 carbon atom. Examples of the alkyl and cycloalkyl groups for $R^1$ include methyl, ethyl, propyl, isopropyl, butyl, pentyl, cyclopentyl, hexyl, cyclohexyl, octyl, and decyl. These alkyl and cycloalkyl groups each may have a substituent.

Examples of the substituent, which the alkyl group or cycloalkyl group for $R^1$ may have, include a halogen atom (for example, fluorine atom, chlorine atom, bromine atom, and iodine atom), an alkyl group having 20 or less carbon atoms (for example, methyl and ethyl), an alkenyl group having 20 or less carbon atoms (for example, vinyl and allyl), a cycloalkyl group having 20 or less carbon atoms (for example, cyclopentyl, cyclohexyl), a cycloalkenyl group having 20 or less carbon atoms (for example, cyclohexenyl), an aryl group having 30 or less carbon atoms (for example, phenyl and naphthyl), a cyano group, a carboxyl group, an alkoxycarbonyl groups having 20 or less carbon atoms (for example, methoxycarbonyl), an aryloxycarbonyl group having 30 or less carbon atoms (for example, phenoxycarbonyl), a carbamoyl group (for example, carbamoyl, N-phenylcarbamoyl, and N,N-dimethylcarbamoyl), an alkylcarbonyl group having 20 or less carbon atoms (for example, acetyl), an arylcarbonyl group having 30 or less carbon atoms (for example, benzoyl), a nitro group, an amino group (for example, amino, dimethylamino, anilino), an acylamino group having 20 or less carbon atoms (for example, acetamido and ethoxycarbonylamino), a sulfonamido group (for example, methanesulfonamido), an imido group (for example, succinimido and phthalimido), an imino group (for example, benzylideneamino), a hydroxyl group, an alkoxy group having 20 or less carbon atoms (for example, methoxy), an aryloxy group having 30 or less carbon atoms (for example, phenoxy), an acyloxy group having 20 or less carbon atoms (for example, acetoxy), an alkylsulfonyloxy group having 20 or less carbon atoms (for example, methanesulfonyloxy), an arylsulfonyloxy group having 30 or less carbon atoms (for example, benzenesulfonyloxy), a sulfo group, a sulfamoyl group (for example, sulfamoyl and N-phenylsulfamoyl), an alkylthio group having 20 or less carbon atoms (for example, methylthio), an arylthio group having 30 or less carbon atoms (for example, phenylthio), an alkylsulfonyl group having 20 or less carbon atoms (for example, methanesulfonyl), an arylsulfonyl group having 30 or less carbon atoms (for example, benzenesulfonyl), and a heterocyclic group. The substituent may be further substituted. When plural substituents are present, they may be the same or different from each other. Also, these substituents may be combined with each other to form a ring. Moreover, the alkyl group(s) or moiety(s) in the substituent may have an unsaturated bond(s) at any position(s) therein.

The aryl group represented by $R^1$ preferably has 6 to 30 carbon atoms, more preferably 6 to 20 carbon atoms, and examples thereof include phenyl and naphthyl, preferably an optionally substituted phenyl group. These aryl groups each may have a substituent as described above for the alkyl or cycloalkyl group.

$R^1$ is preferably an alkyl group, more preferably an unsubstituted alkyl group, further preferably a methyl group or an ethyl group, and most preferably a methyl group.

Q represents a hydrogen atom or an acyl group. The acyl group represented by Q preferably has 1 to 30 carbon atoms, more preferably 1 to 20 carbon atoms, and examples thereof include acetyl, propionyl, pivaloyl, octanoyl, dodecanoyl, and benzoyl. These acyl groups each may have a substituent as described above for the alkyl or cycloalkyl group for $R^1$. Q is preferably an acetyl group or a propionyl group.

The spirocyclic acetal compound represented by formula (II) is preferably a spirocyclic acetal compound represented by formula (A):

(A)

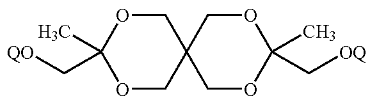

wherein Q represents a hydrogen atom or an acyl group, and Q preferably represents a hydrogen atom, $-COCH_3$, $-COC_2H_5$, $-COCH{=}CH_2$, or $-COC(CH_3){=}CH_2$.

The spirocyclic acetal compound represented by formula (A) is preferably represented by formula (II-1), (II-2), (II-3), or (II-4):

(II-1)

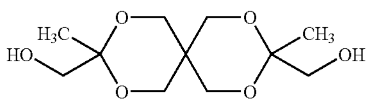

(II-2)

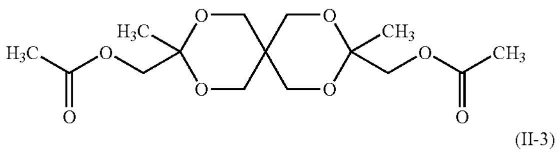

(II-3)

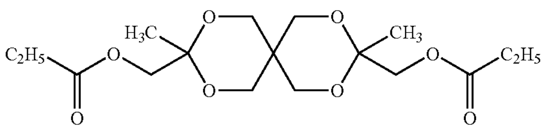

-continued (II-4)

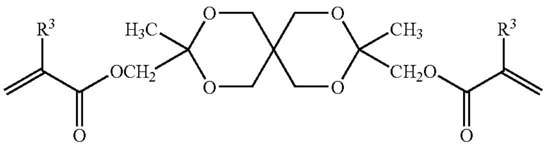

wherein $R^3$ represents a hydrogen atom or a methyl group. $R^3$ is preferably a hydrogen atom.

Next, the method of the present invention of producing the spirocyclic acetal compound is described below.

The spirocyclic acetal compound represented by formula (II) can be produced by subjecting the compound represented by formula (I) and pentaerythritol ($C(CH_2OH)_4$) to dehydration condensation, in the presence of a solid acid catalyst.

In formula (I), $R^1$ and Q each have the same meaning as described in the above for the formula (II), and also have the same preferred range as described above.

In the present invention, as to this dehydration condensation, any method may be used insofar as it can remove or separate the water to be generated, under the reaction conditions. For example, it is preferable to use a method in which water is removed by azeotropic distillation, or a method in which the reaction is run in the presence of a dehydrating agent.

In this case, the amount of pentaerythritol to be used is preferably 0.1 to 5 equivalents, more preferably 0.2 to 1 equivalent, and particularly preferably 0.3 to 0.6 equivalents, to the amount of the compound represented by formula (I).

As the acid catalyst, use may be made of an acid catalyst for general use in acetal-forming reaction, such as p-toluenesulfonic acid monohydrate or pyridinium p-toluenesulfonate, but such a catalyst cannot avoid transesterification or self-condensation. In contrast, a solid acid catalyst is used in the present invention. The solid acid catalyst allows its acidity to be properly controlled and allows the reaction to be controlled by the three-dimensional structure of its surface or in its pores, so that the above-mentioned side reactions, such as transesterification and self-condensation, can be suppressed from occurring.

Examples of the solid acid catalyst include: a substance that has an inorganic or organic matrix and sulfonic acid immobilized in the matrix by a certain method (e.g. Nafion® (trade name) and Amberlite® (trade name, acid type)); nitric acid-oxidized carbon, zeolite (e.g. A-, X- or Y-type, mordenite, erionite, and ZSM-5), aluminum phosphate, and layered clay minerals (e.g. montmorillonite, beidellite, nontronite, saponite, hectorite, and sepiolite). Zeolite and layered clay minerals are more preferred solid acid catalysts, and in particular montmorillonite is preferred.

The solid acid catalyst is preferably used in an amount of 0.1 to 200% by mass, more preferably of 1 to 50% by mass, still more preferably of 5 to 30% by mass, based on the amount of the compound represented by formula (I), depending on the density or acidity of the catalytic site.

When water is removed by azeotropic distillation, a Dean-Stark water separator is preferably used. Also, when removing water by a dehydrating agent, examples of the dehydrating agent include magnesium sulfate, sodium sulfate, zeolite, and molecular sieves. The dehydrating agent is preferably used in an amount identical to or larger than the amount sufficient to retain the water generated in the reaction. The dehydrating agent may be used in the reaction system, or at the outside of the reaction system, for example, by keeping the dehydrating agent in the reflux tube.

The reaction may be conducted without any solvent, or in a solvent. Examples of the solvent that can be used include benzene, toluene, xylene, petroleum ether, N,N-dimethylformamide, N,N-diethylacetamide, 1-methyl-2-pyrrolidone, 1,3-dimethyl-2-imidazolidinone, dimethylsulfoxide (DMSO), sulfolane, carbon tetrachloride, chloroform, hexane, heptane, cycloheptane, and cyclohexane, and mixtures of these solvents. Among these solvents, hexane, heptane, cycloheptane, toluene and xylene are more preferable, and toluene is further preferable. The amount by mass of the solvent to be used is preferably 1 to 100 times and more preferably 2 to 50 times that of the compound represented by formula (I). The reaction temperature is preferably 0 to 200° C. and more preferably 50 to 150° C. The reaction time depends on the type and amount of acid to be used, the type of solvent, and the reaction temperature. The reaction is generally conducted within 12 hours and preferably within 6 hours, by controlling these factors appropriately.

The compound represented by formula (II-1) may be produced by the reaction of pentaerythritol with hydroxyacetone (that is represented by formula (I), in which $R^1$ is a methyl group and Q is a hydrogen atom), under the reaction conditions described above, or alternatively it may be produced by hydrolysis of the compound represented by formula (II) in which Q is an acyl group.

On the other hand, the compound represented by formula (II) in which Q is an acyl group, may be produced by the reaction of pentaerythritol with the compound represented by formula (I) in which Q is an acyl group, under the reaction conditions described above, or alternatively it may be produced by acylation of the compound represented by formula (II-1).

Alkaline conditions are preferably used, when the compound represented by formula (II-1) is produced by hydrolysis of the compound represented by formula (II) in which Q is an acyl group. Besides water, as a solvent, any co-solvent may also be used, such as methanol, ethanol, isopropanol, diethyl ether, tetrahydrofuran, 1,4-dioxane, and acetonitrile. The solvent is preferably used in an amount of 0.5 to 50 parts by mass, more preferably of 1 to 10 parts by mass, based on one part by mass of the compound represented by formula (II) in which Q is an acyl group. When a co-solvent is used, the volume ratio of water/co-solvent is preferably within the range of 1/10 to 10/1, more preferably of 1/3 to 3/1.

Examples of a preferred base include alkali metal hydroxide (e.g. lithium hydroxide, sodium hydroxide, and potassium hydroxide), alkaline earth metal hydroxide (e.g. magnesium hydroxide, calcium hydroxide, and barium hydroxide), and amines (e.g. ammonia, methylamine, dimethylamine, and hydrazine). Sodium hydroxide or potassium hydroxide is more preferred. The base is preferably used in an amount of 1 to 50 equivalents, more preferably of 2 to 10 equivalents, to the amount of the compound represented by formula (II), wherein Q is not a hydrogen atom. The reaction temperature is preferably from 0 to 200° C., more preferably from 20 to 80° C. The reaction time depends on the type and amount of the base to be used, the solvent, and the reaction temperature. These are properly controlled such that the reaction can be completed preferably within 10 hours, more preferably within 5 hours.

In order to produce the compound represented by formula (II) (including the compound represented by formula (II-2), (II-3), or (II-4)) in which Q is an acyl group, by acylation of the compound represented by formula (II-1), use may be made, for example, of a method in which the compound represented by formula (II-1) is allowed to react with a carboxylic acid under neutral to basic conditions (e.g. a method as described in "Jikken Kagaku Koza (Lectures of Experimental Chemistry), 4th. Edition, Vol. 22, Organic Synthesis IV, —Acids, Amino Acids and Peptides—," edited by The Chemical Society of Japan, published by MARUZEN Co. Ltd., p. 45-47), or a method in which the compound represented by formula (II-1) is allowed to react with an acid halide or an acid anhydride under basic conditions (e.g. a method as described in "Jikken Kagaku Koza, 4th. Edition, Vol. 22, Organic Synthesis IV, —Acids, Amino Acids and Peptides—," edited by The Chemical Society of Japan, published by MARUZEN Co. Ltd., p. 50-51). In particular, the compound represented by formula (II-1) is allowed to react with a (meth)acrylic acid derivative (an acid, acid halide, or acid anhydride), to give a di(meth)acrylate represented by formula (II-4), which is useful as a polymerizable bifunctional monomer.

The compound of the present invention is useful as a starting material for polymers and as a crosslinking agent (or a starting material for crosslinking agents). In particular, a polymer having a repeating unit represented by formula (III) is preferred:

(III)

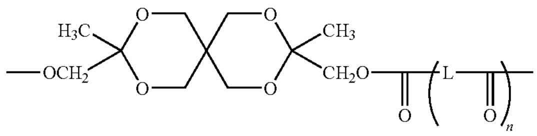

wherein L represents a divalent linking group having at least one carbon atom, and n is 0 or 1.

Preferable examples of L include a linear or branched alkylene group having 1 to 20 carbon atoms (preferably 2 to 10 carbon atoms) (e.g. methylene, ethylene, propylene, butylene, hexylene, and octylene), a cycloalkylene group having 3 to 20 carbon atoms (preferably 5 to 10 carbon atoms) (e.g. cyclopentylene and cyclohexylene), or an arylene group having 6 to 20 carbon atoms (preferably 6 to 12 carbon atoms) (e.g. 1,2-phenylene, 1,3-phenylene, 1,4-phenylene, 1,5-naphthalene, and 2,6-naphthalene). Each of these groups may have a substituent, examples of said substituent include the atoms and groups as described for the alkyl and cycloalkyl groups for $R^1$.

According to the present invention, the polymer having a repeating unit represented by formula (III) can be produced via polymerization, using the spirocyclic acetal compound represented by formula (II), preferably using a spirocyclic acetal compound represented by formula (B), provided that Q in formula (II) is not a (meth)acryloyl group:

(B)

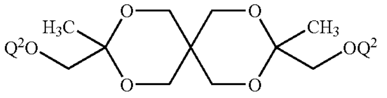

wherein $Q^2$ represents a hydrogen atom, —$COCH_3$, or —$COC_2H_5$. For example, the polymer having the repeating unit represented by formula (III) may be prepared by polycondensation of the compound represented by formula (II-1) and a bifunctional carboxylic acid derivative.

More specifically, a diol represented by formula (II-1) may be subjected to polycondensation with a bifunctional carboxylic acid derivative, thereby to form the polymer having the repeating unit represented by formula (III), for example, according to the method as described in "Jikken Kagaku Koza, 4th. Edition, Vol. 28, Polymer Synthesis," edited by The Chemical Society of Japan, published by MARUZEN Co. Ltd., p. 217-231.

The bifunctional carboxylic acid derivative is preferably an acid halide (e.g. an acid fluoride, an acid chloride, and an acid bromide), and an acid chloride is more preferred.

The polycondensation of the diol represented by formula (II-1) and the bifunctional acid halide may be conducted in the absence of any base, but it is preferably conducted in the presence of a base. Preferred examples of the base include inorganic bases, such as alkali metal hydroxide (e.g. lithium hydroxide, sodium hydroxide, and potassium hydroxide), alkali earth metal hydroxide (e.g. magnesium hydroxide, calcium hydroxide, and barium hydroxide), alkali metal carbonate (e.g. lithium carbonate, sodium carbonate, and potassium carbonate), alkali metal hydrogencarbonate (e.g. lithium hydrogencarbonate, sodium hydrogencarbonate, and potassium hydrogencarbonate), and alkali earth metal carbonate (e.g. magnesium carbonate, calcium carbonate, and barium carbonate); and organic bases, such as pyridine, picoline, lutidine, collidine, quinoline, isoquinoline, triethylamine, diisopropylethylamine, 1,8-diazabicyclo[5.4.0]unde-7-cene, and tetramethylguanidine. Any of the organic bases, such as pyridine, picoline, lutidine, collidine, quinoline, isoquinoline, triethylamine, and diisopropylethylamine, is more preferred. The base is preferably used in an amount of 0.1 to 100 equivalents, more preferably of 2 to 10 equivalents, to the amount of the diol represented by formula (II-1).

In the polycondensation of the diol represented by formula (II-1) and the bifunctional acid halide, the bifunctional acid halide is preferably used in an amount of 0.8 to 1.2 equivalents, more preferably of 0.95 to 1.05 equivalents, to the amount of the diol represented by formula (II-1). The polycondensation of the diol represented by formula (II-1) and the bifunctional acid halide may be carried out in the absence of any solvent or may be carried out in a solvent, preferably at a temperature of −20 to 200° C., more preferably of 0 to 100° C. Preferred examples of the solvent include benzene, toluene, xylene, petroleum ether, N,N-dimethylformamide, N,N-diethylacetamide, 1-methyl-2-pyrrolidone, 1,3-dimethyl-2-imidazolidinone, dimethylsulfoxide (DMSO), sulfolane, carbon tetrachloride, chloroform, hexane, heptane, cyclohexane, and a mixed solvent thereof.

According to the method of the present invention, by-product formation can be remarkably suppressed, and 3,9-dialkyl (or dicycloalkyl or diaryl)-3,9-bis[acyloxymethyl (or hydroxymethyl)]-2,4,8,10-tetraoxaspiro[5,5]undecane can be efficiently produced, which is useful as a starting material for polymers and as a crosslinking agent (or a starting material for crosslinking agents). Further, the present invention provides novel compounds: 3,9-dimethyl-3,9-bis(hydroxymethyl)-2,4,8,10-tetraoxaspiro[5,5]undecane, 3,9-dimethyl-3,9-bis(acetyloxymethyl)-2,4,8,10-tetraoxaspiro[5,5]undecane, 3,9-dimethyl-3,9-bis(propionyloxymethyl)-2,4,8,10-tetraoxaspiro[5,5]undecane, and 3,9-dimethyl-3,9-bis[(meth)acryloyloxymethyl]-2,4,8,10-tetraoxaspiro[5,5]undecane; and also provides polyesters which can be obtained from, as starting materials, 3,9-dimethyl-3,9-bis(hydroxymethyl)-2,4,8,10-tetraoxaspiro[5,5]undecane.

The present invention will be described in more detail based on the following examples, but the invention is not meant to be limited thereto.

EXAMPLES

<1> Preparation of 3,9-dimethyl-3,9-bis(propionyloxymethyl)-2,4,8,10-tetraoxaspiro[5,5]undecane (a Compound Represented by Formula (II-3)) (Examples 1 and 2, and Comparative Examples 1 and 2)

Comparative Example 1

To a solution of hydroxyacetone (190 g, 2.56 mol) and pyridine (210 ml, 2.6 mol) in ethyl acetate (1 L), propionyl chloride (197 g, 2.1 mol) was added dropwise at 5° C. The reaction liquid was stirred at room temperature for one hour, and then poured into water (700 ml). After phase separation, the organic layer was washed twice with a 1–N aqueous hydrochloric acid (700 ml), twice with water (700 ml), and once with saturated brine (500 ml), and dried over magnesium sulfate. After the magnesium sulfate was filtered out, the solvent was distilled off under reduced pressure, to obtain propionyloxyacetone (177 g, 1.36 mol). The thus-obtained propionyloxyacetone was used in the next process, without further purification.

A solution of propionyloxyacetone (10 g, 76.8 mmol), pentaerythritol (5.22 g, 38.4 mmol), and p-toluenesulfonic acid monohydrate (0.76 g, 4 mmol) in toluene (200 ml) was stirred under reflux for 3 hours, while water was removed using a Dean-Stark water separator. After cooling to room temperature, the reaction liquid was poured into ethyl acetate (300 ml)/an aqueous sodium hydrogencarbonate solution (350 ml). After phase separation, the organic layer was washed twice with water (200 ml), and once with saturated brine (200 ml), and then dried over sodium sulfate. After the sodium sulfate was filtered out, the solvent was distilled off under reduced pressure, to obtain 11.6 g of a concentrate residue. As a result of measurement of NMR spectra of the concentrate residue, it was found that the concentrate residue was a mixture mainly composed of propionyloxyacetone (starting material), 3,9-dimethyl-3,9-bis(propionyloxymethyl)-2,4,8,10-tetraoxaspiro[5,5]undecane (target substance), and 2-methyl-2,5,5-tris(propionyloxymethyl)-[1,3]dioxane (by-product) (the ratio was (starting material):(target substance):(by-product)≈1:4:1). The concentrate residue was purified by column chromatography (eluent: ethyl acetate/hexane=1/2), to give 3,9-dimethyl-3,9-bis(propionyloxymethyl)-2,4,8,10-tetraoxaspiro[5,5]undecane (7.5 g, 20.8 mmol, yield 54%).

$^1H$ NMR ($CDCl_3$): δ 4.21-4.12 (m, 4H), 3.89-3.67 (m, 8H), 2.39 (q, J=7.5 Hz, 4H), 1.40 (s, 6H), 1.16 (t, J=7.5 Hz, 6H)

m.p.=55-56° C.

Comparative Example 2

A solution of propionyloxyacetone (10 g, 76.8 mmol), pentaerythritol (5.22 g, 38.4 mmol), and pyridinium p-toluenesulfonate (1.0 g, 4 mmol) in toluene (200 ml) was stirred under reflux for 6 hours, while water was removed using a Dean-Stark water separator. After cooling to room temperature, the reaction liquid was poured into ethyl acetate (300 ml)/an aqueous sodium hydrogencarbonate solution (350 ml). After phase separation, the organic layer was washed twice with water (200 ml), and once with saturated brine (200 ml), and then dried over sodium sulfate. After the sodium sulfate was filtered out, the solvent was distilled off under reduced pressure, to obtain 11.0 g of a concentrate residue. As a result of measurement of NMR spectra of the concentrate residue, it was found that the by-product of Comparative Example 1 (2-methyl-2,5,5-tris(propionyloxymethyl)-[1,3]dioxane) was hardly detected, while other by-products were formed, and that the starting material propionyloxyacetone remained at a similar level to that in Comparative Example 1. The concentrate residue was purified by column chromatography (eluent: ethyl acetate/hexane=1/2), to give 3,9-dimethyl-3,9-bis(propionyloxymethyl)-2,4,8,10-tetraoxaspiro[5,5]undecane (7.3 g, 20.3 mmol, yield 53%).

Example 1

A solution of propionyloxyacetone (10 g, 76.8 mmol), pentaerythritol (5.22 g, 38.4 mmol), and zeolite (1.5 g) in toluene (200 ml) was stirred under reflux for 6 hours, while water was removed using a Dean-Stark water separator. After the reaction liquid was cooled to room temperature, cerite filtration was conducted, and then the solvent was distilled off under reduced pressure, to obtain 10.8 g of a concentrate residue. As a result of measurement of NMR spectra of the concentrate residue, it was found that the by-products occurred in Comparative Examples 1 or 2 were hardly detected and that the concentrate residue was a mixture mainly composed of propionyloxyacetone (starting material) and 3,9-dimethyl-3,9-bis(propionyloxymethyl)-2,4,8,10-tetraoxaspiro[5,5]undecane (target substance) (the ratio was (starting material):(target substance)≈1:8). The concentrate residue was recrystallized from ethyl acetate/hexane, to give 3,9-dimethyl-3,9-bis(propionyloxymethyl)-2,4,8,10-tetraoxaspiro[5,5]undecane (8.5 g, 23.6 mmol, yield 61%).

Example 2

A solution of propionyloxyacetone (10 g, 76.8 mmol), pentaerythritol (5.22 g, 38.4 mmol), and montmorillonite (Montmorillonite K10, trade name, manufactured by Aldrich) (1.5 g) in toluene (200 ml) was stirred under reflux for 6 hours, while water was removed using a Dean-Stark water separator. After the reaction liquid was cooled to room temperature, cerite filtration was conducted, and then the solvent was distilled off under reduced pressure, to obtain 11.5 g of a concentrate residue. As a result of measurement of NMR spectra of the concentrate residue, it was found that the by-products occurred in Comparative Examples 1 or 2 were hardly detected and that the concentrate residue was a mixture mainly composed of propionyloxyacetone (starting material) and 3,9-dimethyl-3,9-bis(propionyloxymethyl)-2,4,8,10-tetraoxaspiro[5,5]undecane (target substance) (the ratio was (starting material):(target substance)≈1:10). The concentrate residue was recrystallized from ethyl acetate/hexane, to give 3,9-dimethyl-3,9-bis(propionyloxymethyl)-2,4,8,10-tetraoxaspiro[5,5]undecane (9.5 g, 26.4 mmol, yield 69%).

As is apparent from the results of Examples 1 and 2 and Comparative Examples 1 and 2, it was found that the method of the present invention using a solid acid catalyst can produce a spirocyclic acetal compound in good yield, with almost no formation of any by-products.

<2> Preparation of 3,9-dimethyl-3,9-bis(acetyloxymethyl)-2,4,8,10-tetraoxaspiro[5,5]undecane (a Compound Represented by Formula (II-2)) (Examples 3 and 4, and Comparative Example 3)

Comparative Example 3

To a solution of hydroxyacetone (100 g, 1.35 mol) and pyridine (121 ml, 1.5 mol) in ethyl acetate (1 L), acetyl chloride (96 ml, 1.35 mol) was added dropwise at 5° C. The reaction liquid was stirred at room temperature for one hour, and then poured into 1-N aqueous hydrochloric acid (400 ml). After phase separation, the organic layer was washed with water (300 ml) and then saturated brine (300 ml), and dried over magnesium sulfate. After the magnesium sulfate was filtered out, the solvent was distilled off under reduced pressure, to obtain acetoxyacetone (40 g, 0.34 mol). The thus-obtained acetyloxyacetone was used in the next process, without further purification.

A solution of acetyloxyacetone (28.3 g, 244 mmol), pentaerythritol (16.6 g, 122 mmol), and p-toluenesulfonic acid monohydrate (1.74 g, 9.2 mmol) in toluene (200 ml) was stirred under reflux for 3 hours, while water was removed using a Dean-Stark water separator. After cooling to room temperature, the reaction liquid was poured into ethyl acetate (300 ml)/an aqueous sodium hydrogencarbonate solution (350 ml). After phase separation, the organic layer was washed twice with water (200 ml), and once with saturated brine (200 ml), and then dried over sodium sulfate. After the sodium sulfate was filtered out, the solvent was distilled off under reduced pressure, to obtain 31.5 g of a concentrate residue. As a result of measurement of NMR spectra of the concentrate residue, it was found that the concentrate residue was a complicated mixture containing the starting material and the target substance. The concentrate residue was purified by column chromatography (eluent: ethyl acetate/hexane=1/2), to give 3,9-dimethyl-3,9-bis(acetyloxymethyl)-2,4,8,10-tetraoxaspiro[5,5]undecane (7.6 g, 22.9 mmol, yield 19%).

$^1$H NMR ($CDCl_3$): δ 4.19-4.10 (m, 4H), 3.91-3.66 (m, 8H), 2.10 (s, 6H), 1.41 (s, 6H)

m.p.=66-67° C.

Example 3

A solution of acetyloxyacetone (8.9 g, 76.8 mmol), pentaerythritol (5.22 g, 38.4 mmol), and zeolite (1.5 g) in toluene (200 ml) was stirred under reflux for 6 hours, while water was removed using a Dean-Stark water separator. After the reaction liquid was cooled to room temperature, cerite filtration was conducted, and then the solvent was distilled off under reduced pressure, to obtain 10.3 g of a concentrate residue. As a result of measurement of NMR spectra of the concentrate residue, it was found that the concentrate residue was a mixture mainly composed of acetyloxyacetone (starting material) and 3,9-dimethyl-3,9-bis(acetyloxymethyl)-2,4,8,10-tetraoxaspiro[5,5]undecane (target substance) (the ratio was (starting material):(target substance)≈1:9). The concentrate residue was recrystallized from ethyl acetate/hexane, to give 3,9-dimethyl-3,9-bis(acetyloxymethyl)-2,4,8,10-tetraoxaspiro[5,5]undecane (8.3 g, 25.0 mmol, yield 65%).

Example 4

A solution of acetyloxyacetone (8.9 g, 76.8 mmol), pentaerythritol (5.22 g, 38.4 mmol), and montmorillonite (Montmorillonite K10) (1.5 g) in toluene (200 ml) was stirred under reflux for 6 hours, while water was removed using a Dean-Stark water separator. After the reaction liquid was cooled to room temperature, cerite filtration was conducted, and then the solvent was distilled off under reduced pressure, to obtain 10.7 g of a concentrate residue. As a result of measurement of NMR spectra of the concentrate residue, it was found that the concentrate residue was a mixture mainly composed of acetyloxyacetone (starting material) and 3,9-dimethyl-3,9-bis(acetyloxymethyl)-2,4,8,10-tetraoxaspiro[5,5]undecane (target substance) (the ratio was (starting material):(target substance)≈1:9). The concentrate residue was recrystallized from ethyl acetate/hexane, to give 3,9-dimethyl-3,9-bis(acetyloxymethyl)-2,4,8,10-tetraoxaspiro[5,5]undecane (8.5 g, 25.6 mmol, yield 67%).

As is apparent from the results of Examples 3 and 4 and Comparative Example 3, it was found that in contrast to Comparative Example 3 in which the yield of the target substance was conspicuously low, according to the method of the present invention using a solid acid catalyst, a spirocyclic acetal compound was able to be prepared in remarkably higher yield, with almost no occurrence of any by-products.

<3> Preparation of 3,9-dimethyl-3,9-bis(hydroxymethyl)-2,4,8,10-tetraoxaspiro[5,5]undecane (a Compound Represented by Formula (II-1)) (Example 5, and Comparative Example 4)

Example 5

A solution of hydroxyacetone (5.7 g, 76.8 mmol), pentaerythritol (5.22 g, 38.4 mmol), and montmorillonite (Montmorillonite K10) (1.5 g) in toluene (200 ml) was stirred under reflux for 6 hours, while water was removed using a Dean-Stark water separator. After the reaction liquid was cooled to 50° C., cerite filtration was conducted, and then the solvent was distilled off under reduced pressure, to obtain 9.4 g of a concentrate residue. The concentrate residue was purified by column chromatography (eluent: dichloromethane/methanol=10/1), to give 3,9-dimethyl-3,9-bis(hydroxymethyl)-2,4,8,10-tetraoxaspiro[5,5]undecane (6.1 g, 24.5 mmol, yield 64%).

$^1$H NMR ($DMSO_{d-6}$): δ 4.71 (bs, 2H), 3.78-3.57 (m, 8H), 3.33 (bs, 4H), 1.27 (s, 6H)

m.p.=127-128° C.

Comparative Example 4

A solution of hydroxyacetone (5.7 g, 76.8 mmol), pentaerythritol (5.22 g, 38.4 mmol), and p-toluenesulfonic acid monohydrate (0.76 g, 4 mmol) in toluene (200 ml) was stirred under reflux for 3 hours, while water was removed using a Dean-Stark water separator. The progress of reaction was monitored by TLC, and the formation of a large number of by-products was observed, while the target 3,9-dimethyl-3,9-bis(hydroxymethyl)-2,4,8,10-tetraoxaspiro[5,5]undecane was produced only in a very small amount.

As is apparent from the results of Example 5 and Comparative Example 4, it was been found that, in contrast to Comparative Example 3 in which a large number of by-products were formed while only a very small amount of the target substance was obtained, the method of the present invention using a solid acid catalyst was able to produce a spirocyclic acetal compound in good yield.

<4> Preparation of 3,9-dimethyl-3,9-bis(hydroxymethyl)-2,4,8,10-tetraoxaspiro[5,5]undecane (a Compound Represented by Formula (II-1))

Example 6

To a solution of sodium hydroxide (3 g, 0.075 mol) in water (25 ml) and methanol (25 ml), 3,9-dimethyl-3,9-bis(propionyloxymethyl)-2,4,8,10-tetraoxaspiro[5,5]undecane (6.5 g, 18 mmol) was slowly added, followed by stirring for 40 minutes at 60° C. After the solvent was distilled off under reduced pressure, the resultant concentrate residue was dissolved in acetonitrile/brine. The separated-off organic layer was concentrated under reduced pressure, and then ethyl acetate was added thereto. After the insoluble material was filtered out, the resultant filtrate was concentrated again under reduced pressure. The resultant concentrate residue was recrystallized from ethyl acetate/hexane, to give 3,9-dimethyl-3,9-bis(hydroxymethyl)-2,4,8,10-tetraoxaspiro[5,5]undecane (3.4 g, 13.7 mmol, yield 76%).

As is apparent from the results of Example 6, it was found that the compound represented by formula (II-1) can also be produced in good yield by hydrolysis of the compound represented by formula (II-3).

<5> Preparation of 3,9-dimethyl-3,9-bis(acryloyloxymethyl)-2,4,8,10-tetraoxaspiro[5,5]undecane (a Compound Represented by Formula (II-4) ($R^3$=H))

Example 7

To a solution of 3,9-dimethyl-3,9-bis(hydroxymethyl)-2,4,8,10-tetraoxaspiro[5,5]undecane (2.5 g) and pyridine (2.1 ml) in ethyl acetate (50 ml), acryloyl chloride (2.0 ml) was added dropwise. The reaction liquid was stirred at room temperature for 5 hours, and then poured into ethyl acetate (100 ml)/1-N aqueous hydrochloric acid (100 ml), to be separated into organic and aqueous layers. The resultant organic layer was washed with sodium hydrogencarbonate water (100 ml), water (100 ml×2 times), and saturated brine (100 ml), and then dried over sodium sulfate. After the sodium sulfate was filtered out, the solvent was distilled off under reduced pressure. The resultant concentrate residue was purified by column chromatography (eluent: ethyl acetate/hexane=1/2), to give 3,9-dimethyl-3,9-bis(acryloyloxymethyl)-2,4,8,10-tetraoxaspiro[5,5]undecane (3.1 g, yield 86%).

$^1$H NMR ($CDCl_3$): δ 6.45 (dd, J=17.6 Hz, 1.6 Hz, 2H), 6.17 (dd, J=17.6 Hz, 10.4 Hz, 2H), 5.87 (dd, J=10.4 Hz, 1.6 Hz, 2H), 4.27 (d, J=11.6 Hz, 2 H), 4.22 (d, J=11.6 Hz, 2H), 3.84 (dd, J=35.6 Hz, 11.6 Hz, 4H), 3.73 (dd, J=25.8 Hz, 11.6 Hz, 4H), 1.43 (s, 6H)

Example 8

Preparation of a polymer having a repeating unit represented by the following formula:

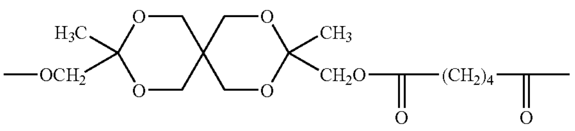

To a solution of 3,9-dimethyl-3,9-bis(hydroxymethyl)-2,4,8,10-tetraoxaspiro[5,5]undecane (1.25 g) and pyridine (0.9 ml) in ethyl acetate (50 ml), adipic acid chloride (0.73 ml) was added dropwise. The reaction liquid was stirred at room temperature for one hour, and further stirred at 60° C. for one hour. After cooling to room temperature, the precipitated crystal was filtered, and washed sufficiently with water. The thus-obtained crystal was dissolved in dichloromethane (100 ml). After the insoluble material was filtered out, the filtrate was concentrated under reduced pressure. The concentrate residue (1.62 g) was dissolved in dichloromethane (16 ml), and reprecipitated from isopropanol (1 L), to give a white polymer (1.3 g). In FT-IR analysis, the absorption of a hydroxyl group almost disappeared, while the absorption of an ester group was identified. Further, NMR measurement also revealed that the thus-obtained polymer had the above-shown repeating unit.

$^1$H NMR ($CDCl_3$): δ 4.21-4.10(m, 4H), 3.87-3.3.53 (m, 8H), 2.39 (bs, 4H), 1.67 (bs, 4H), 1.40 (s, 6H)

Using a gel permeation chromatograph analyzer, manufactured by Tosoh Corporation (HLC-8220GPC, trade name), the number average molecular weight (Mn) and mass average molecular weight (Mw) of the thus-obtained polymer were measured. As a result, Mn was 2,729 and Mw was 3,850, respectively, as the values equivalent to those of polystyrene.

Example 9

Preparation of a polymer having a repeating unit represented by the following formula:

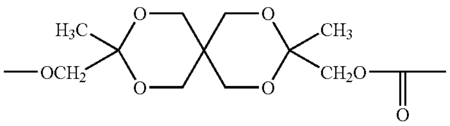

To a solution of 3,9-dimethyl-3,9-bis(hydroxymethyl)-2,4,8,10-tetraoxaspiro[5,5]undecane (3.75 g) and pyridine (2.7 ml) in ethyl acetate (120 ml), a solution of triphosgene (1.5 g) in ethyl acetate (30 ml) was added dropwise. The reaction liquid was stirred at room temperature for one hour, and further stirred at 60° C. for one hour. After cooling to room temperature, the reaction liquid was poured into ethyl acetate (100 ml)/1-N aqueous hydrochloric acid (100 ml), to be separated into organic and aqueous layers. The resultant organic layer was washed with sodium hydrogencarbonate water (100 ml), water (100 ml×2 times), and saturated brine (100 ml), and then dried over magnesium sulfate. After the magnesium sulfate was filtered out, the solvent was distilled off under reduced pressure. The concentrate residue (3.56 g) was dissolved in dichloromethane (36 ml), and reprecipitated from isopropanol (1.8 L), to give a white polymer (2.5 g). In FT-IR analysis, the absorption of a hydroxyl group almost disappeared, while the absorption of carbonate was identified. Further, NMR measurement also revealed that the thus-obtained polymer had the above-shown repeating unit.

$^1$H NMR ($CDCl_3$): δ 4.24-4.15 (m, 4H), 3.87-3.3.53 (m, 8H), 1.42 (s, 6H)

Using a gel permeation chromatograph analyzer, manufactured by Tosoh Corporation (HLC-8220GPC), the number average molecular weight (Mn) and mass average molecular weight (Mw) of the thus-obtained polymer were measured. As a result, Mn was 3,916 and Mw was 5,036, respectively, as the values equivalent to those of polystyrene.

<6> Evaluation of 3,9-dimethyl-3,9-bis(acryloyloxymethyl)-2,4,8,10-tetraoxaspiro[5,5]undecane (a Compound Represented by Formula (II-4) ($R^3$=H)) as a Crosslinking Agent Example 10

A hard coat layer was formed on a thermoplastic norbornene-series resin film in the same manner as in Examples 1 and 2 in JP-A-2004-331795, except that 3,9-dimethyl-3,9-bis(acryloyloxymethyl)-2,4,8,10-tetraoxaspiro[5,5]undecane was used in the same mass, in place of tricyclodecanedimethylol diacrylate in Example 2 of JP-A-2004-331795. The results of the outer appearance, the light transmittance at 400 nm according to JIS-K-7105, the cross-cut peeling test according to JIS-K-5400, and the high-temperature high-humidity endurance test at 85° C. and 85% RH for 1,000 hours, were similar to the results of Example 2 in JP-A-2004-331795.

Example 11

A hard coat layer was formed on a polycarbonate sheet in the same manner as in Example 1 in JP-A-2006-63 162, except that 3,9-dimethyl-3,9-bis(acryloyloxymethyl)-2,4,8,10-tetraoxaspiro[5,5]undecane was used in the same mass, in place of 1,6-hexanediol diacrylate in Example 1 of JP-A-2006-63162. The results of the outer appearance, the weatherability test according to JIS-K-5600, the taper abrasion test according to ASTM D1044, the formability test, and the adhesion test according to JIS-K-5400, were similar to the results of Example 1 in JP-A-2006-63162.

From these results, it was found that 3,9-dimethyl-3,9-bis(acryloyloxymethyl)-2,4,8,10-tetraoxaspiro[5,5]undecane is useful as a crosslinking agent excellent in transparency, outer appearance, adhesion, durability, and the like.

<7> Evaluation of Usefulness of the Polymer Having a Repeating Unit represented by Formula (III)

Example 12

A piece of the polymer prepared in Example 8 was sandwiched between cover glasses, manufactured by Matsunami Glass Ind., Ltd. (18 mm×18 mm, thickness 0.12 to 0.17 mm), followed by heating gradually, and the resultant polymer was melted at 110 to 120° C. The thus-melted polymer was pressed and extended uniformly between the cover glasses, followed by cooling to room temperature. As a result, the resultant cover glasses were transparent and strongly bonded to each other and not capable of being peeled off from each other.

Comparative Example 5

The test was conducted in the same manner as in Example 12, except for using a polyester of bisphenol A and adipic acid (Mw≈10,000). As a result, the polymer was melted near 150° C. and transiently became transparent but became whitish when cooled to room temperature, and it was possible to easily separate the cover glasses from each other.

From the results of the above-mentioned Examples 8 to 12 and Comparative Example 5, it can be concluded that the polymer of the present invention having the repeating unit represented by formula (III) can be used in a variety of applications, and, for example, is useful as a transparent adhesive for glass. Further, since the polymer having the repeating unit represented by formula (III) is a polyester with a cyclic structure having no aromatic ring, it can be expected that said polymer would have a variety of unique characteristics, e.g. transparency, weather resistance, heat resistance, and biodegradability.

Having described our invention as related to the present embodiments, it is our intention that the invention not be limited by any of the details of the description, unless otherwise specified, but rather be construed broadly within its spirit and scope as set out in the accompanying claims.

What we claim is:

1. A method of producing a spirocyclic acetal compound represented by formula (II), comprising the step of:

subjecting a compound represented by formula (I) and pentaerythritol to dehydration condensation, in the presence of a solid acid catalyst, (I)

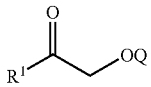

-continued (II)

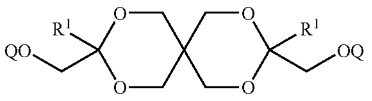

wherein $R^1$ represents an alkyl group, a cycloalkyl group or an aryl group, in which each of these groups may have a substituent; and Q represents a hydrogen atom or an acyl group.

2. The method according to claim 1, wherein the solid acid catalyst is zeolite or a layered clay mineral.

3. The method according to claim 1, wherein the solid acid catalyst is a layered clay mineral.

4. The method according to claim 3, wherein the layered clay mineral is montmorillonite.

5. The method according to claim 1, wherein $R^1$ is a methyl group.

6. A spirocyclic acetal compound represented by Formula (II):

(II)

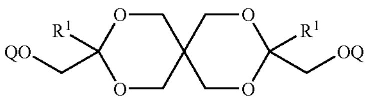

wherein $R^1$ represents an alkyl group, a cycloalkyl group or an aryl group; and Q represents a hydrogen atom, $—COCH_3$, $—COC_2H_5$, $—COCH{=}CH_2$, or $—COC(CH_3){=}CH_2$.

7. The spirocyclic acetal compound according to claim 6, wherein the compound represented by formula (II) is a compound represented by formula (II-1), (II-2), or (II-3):

(II-1)

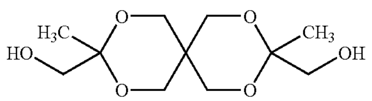

(II-2)

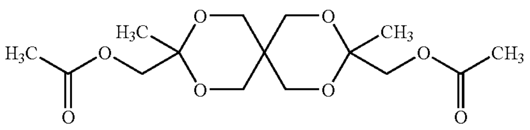

(II-3)

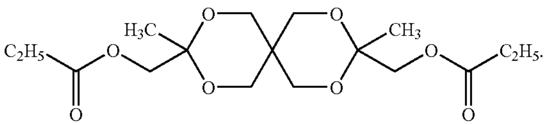

8. The spirocyclic acetal compound according to claim 6, wherein the compound represented by formula (II) is a compound represented by formula (II-4):

(II-4)

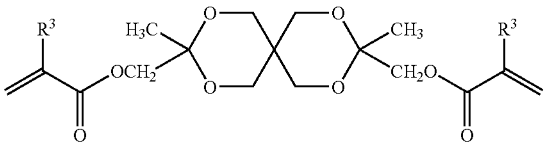

wherein $R^3$ represents a hydrogen atom or a methyl group.

9. A polymer having a repeating unit represented by formula (III):

(III)

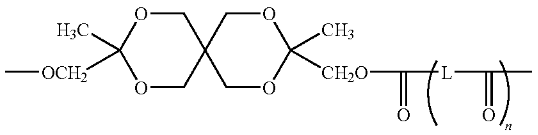

wherein L represents a divalent linking group having at least one carbon atom, and n represents 0 or 1.

10. A method of producing a polymer having a repeating unit represented by formula (III), comprising the steps of:

subjecting a spirocyclic acetal compound represented by formula (B), to polymerization:

(B)

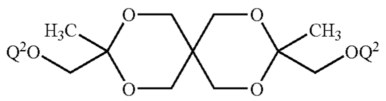

wherein $Q^2$ represents a hydrogen atom, $—COCH_3$, or $—COC_2H_5$;

(III)

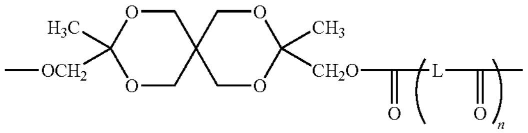

wherein L represents a divalent linking group having at least one carbon atom, and n represents 0 or 1.

* * * * *